US00PP33886P2

(12) United States Plant Patent
van Langen

(10) Patent No.: US PP33,886 P2
(45) Date of Patent: Jan. 18, 2022

(54) ***ECHEVERIA* PLANT NAMED 'AMIECH2103**

(50) Latin Name: ***Echeveria setosa 'Oliver'* x *Echeveria purpusorum* A. Berger**
Varietal Denomination: AMIECH2103

(71) Applicant: Novoami B.V., Heerhugowaard (NL)

(72) Inventor: Gerard van Langen, Heerhugowaard (NL)

(73) Assignee: Novoami B.V., Heerhugowaard (NL)

( * ) Notice: Subject to any disclaimer, the term of this patent is extended or adjusted under 35 U.S.C. 154(b) by 0 days.

(21) Appl. No.: 17/300,642

(22) Filed: Sep. 8, 2021

(30) Foreign Application Priority Data

Apr. 26, 2021 (QZ) ..... 2021/1150

(51) Int. Cl.
*A01H 5/02* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32; A01H 5/02; A01H 5/00
See application file for complete search history.

*Primary Examiner* — Keith O. Robinson
(74) *Attorney, Agent, or Firm* — Samuel R. McCoy, Jr.

(57) ABSTRACT

A new and distinct *Echeveria* hybrid plant named 'AMIECH2103' which is characterized by a flattened globular plant profile with foliage loosely arranged in a basal rosette, a relative abundance of long and narrow foliage that is conspicuously curled upward, dark green foliage that is tipped greyed-orange to brown and fades to a light shade of yellow-green towards the base, and the stability of these characteristics from generation to generation.

4 Drawing Sheets

Latin name of the genus and species: The Latin name of the genus and species of the novel variety disclosed herein is *Echeveria setosa* 'Oliver' x *Echeveria purpusorum* A. Berger.

Variety denomination: The inventive variety of *Echeveria* hybrid disclosed herein has been given the variety denomination 'AMIECH2103'.

CROSS REFERENCE TO RELATED APPLICATIONS

This application claims priority to the Community Plant Variety Rights application number 2021/1150, filed Apr. 26, 2021, which is herein incorporated by reference.

BACKGROUND OF THE INVENTION

Parentage: 'AMIECH2103' is an interspecific hybrid seedling selection resulting from the controlled pollination of an *Echeveria setosa* 'Oliver' plant (not patented), the seed parent, with an unnamed *Echeveria purpusorum* plant (not patented), the pollen parent. The crossing was made by the inventor in the spring of 2017 at a commercial greenhouse in Heerhugowaard, the Netherlands. In summer of 2018, one seedling was observed which exhibited unique growth and foliage characteristics. The seedling was isolated for further evaluation in order to confirm the distinctness and stability of the characteristics first observed. Upon confirmation of distinctness and stability, 'AMIECH2103' was selected for commercialization.

Asexual Reproduction: Asexual reproduction of the new cultivar 'AMIECH2103', by way of rooting leaf cuttings, was first initiated in the autumn of 2018 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMIECH2103' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2103'. These characteristics in combination distinguish 'AMIECH2103' as a new and distinct *Echeveria* hybrid cultivar:

1. 'AMIECH2103' exhibits a flattened globular plant profile with foliage loosely arranged in a basal rosette which eventually forms a short, unbranched stem with age; and
2. 'AMIECH2103' exhibits a relative abundance of long, narrow oblanceolate foliage that is conspicuously curled upward; and
3. 'AMIECH2103' exhibits mature foliage with ciliate margins and a lightly pubescent abaxial surface; and
4. 'AMIECH2103' exhibits dark green foliage that is tipped greyed-orange to brown and fades to a light shade of yellow-green towards the base.

BOTANICAL DESCRIPTION OF THE PLANT

Figure 1:
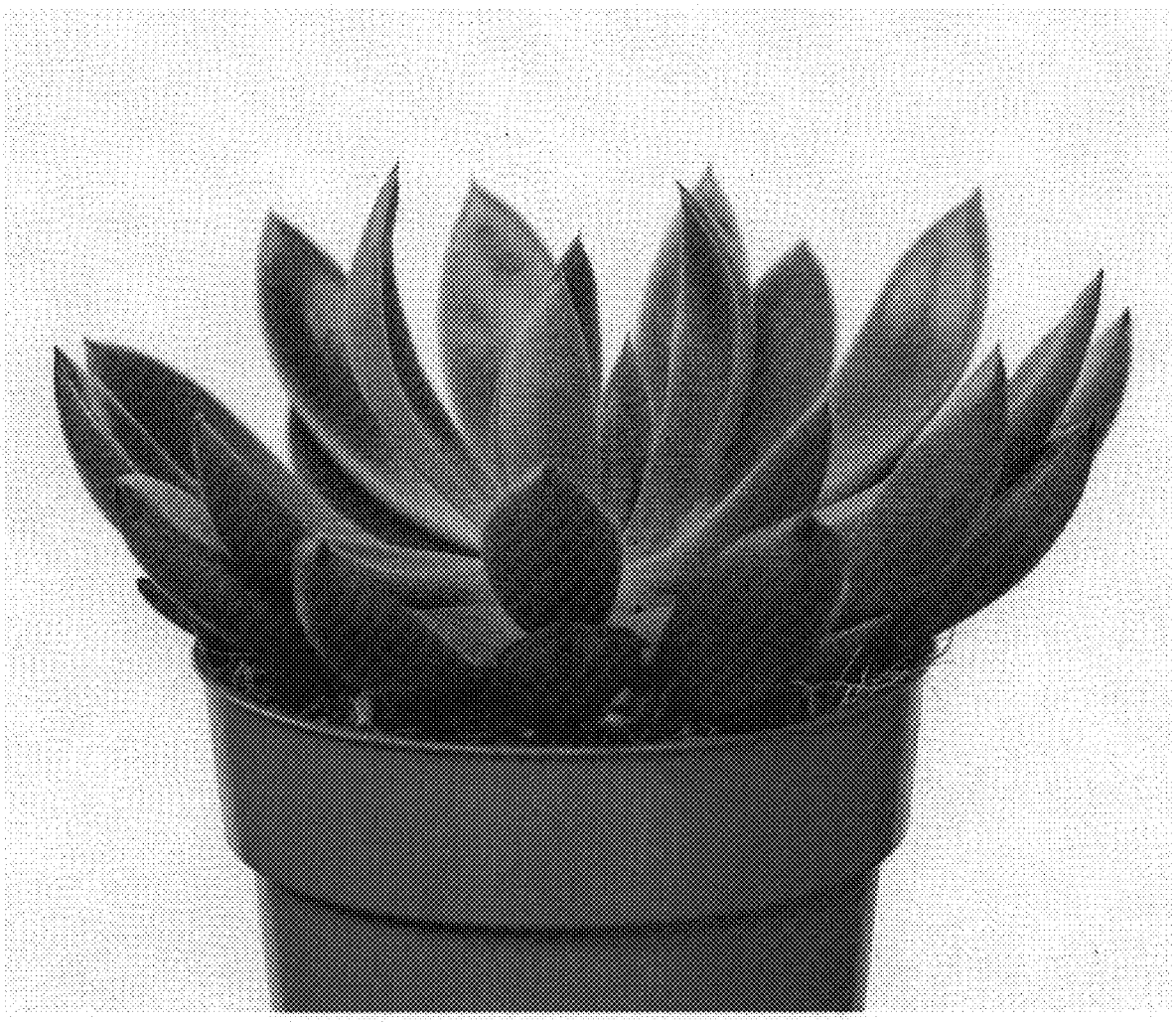
FIG. 1 illustrates, as nearly true as it is reasonably possible to make the same in color photographs of this type, an exemplary plant of 'AMIECH2103' grown in a commercial greenhouse in Heerhugowaard, the Netherlands. This plant is approximately 26 week-old, shown planted in an 8.5 cm container.
Figure 2:
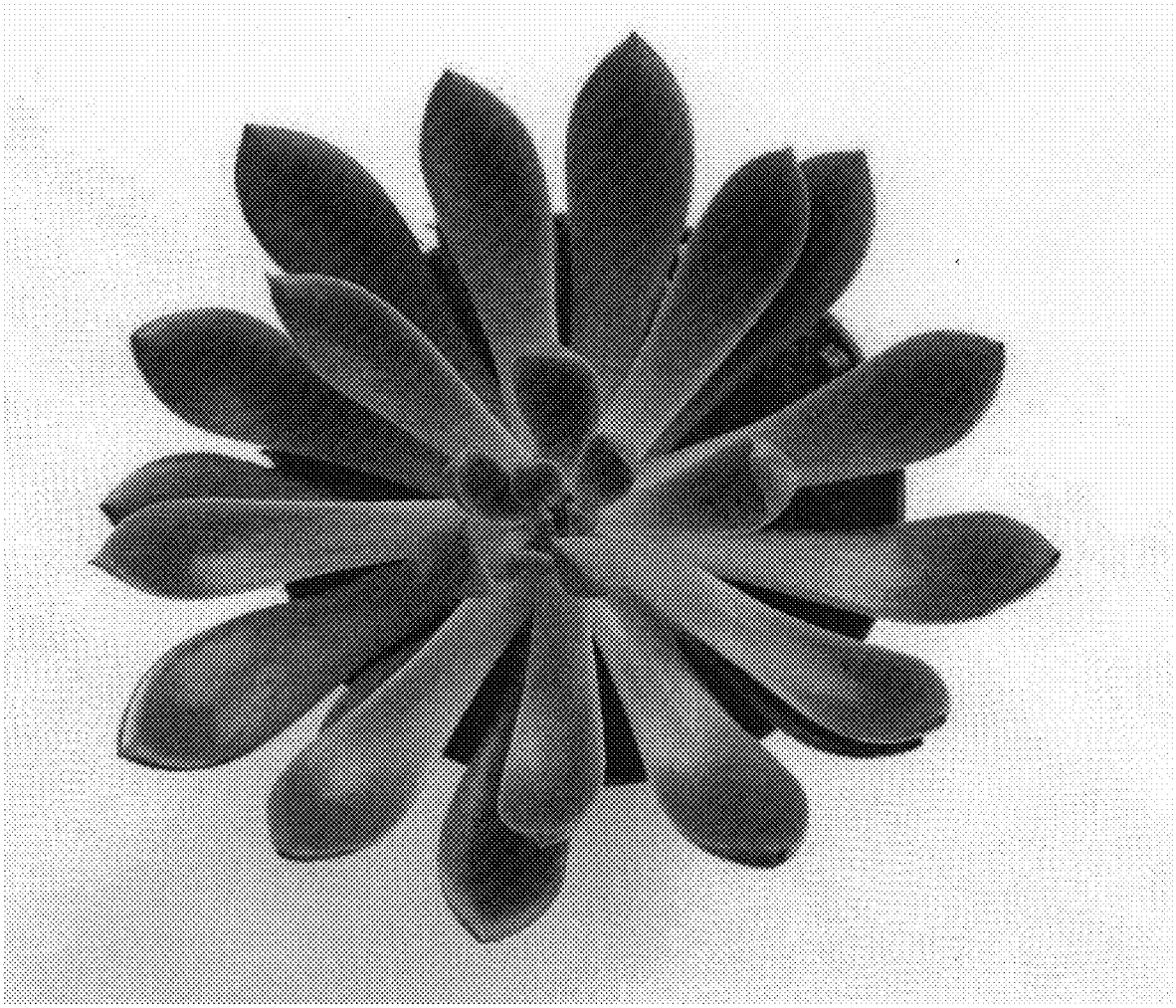
FIG. 2 illustrates, as nearly true as it is reasonably possible to make the same in color photographs of this type, the typical foliage arrangement of 'AMIECH2103.
Figure 3:
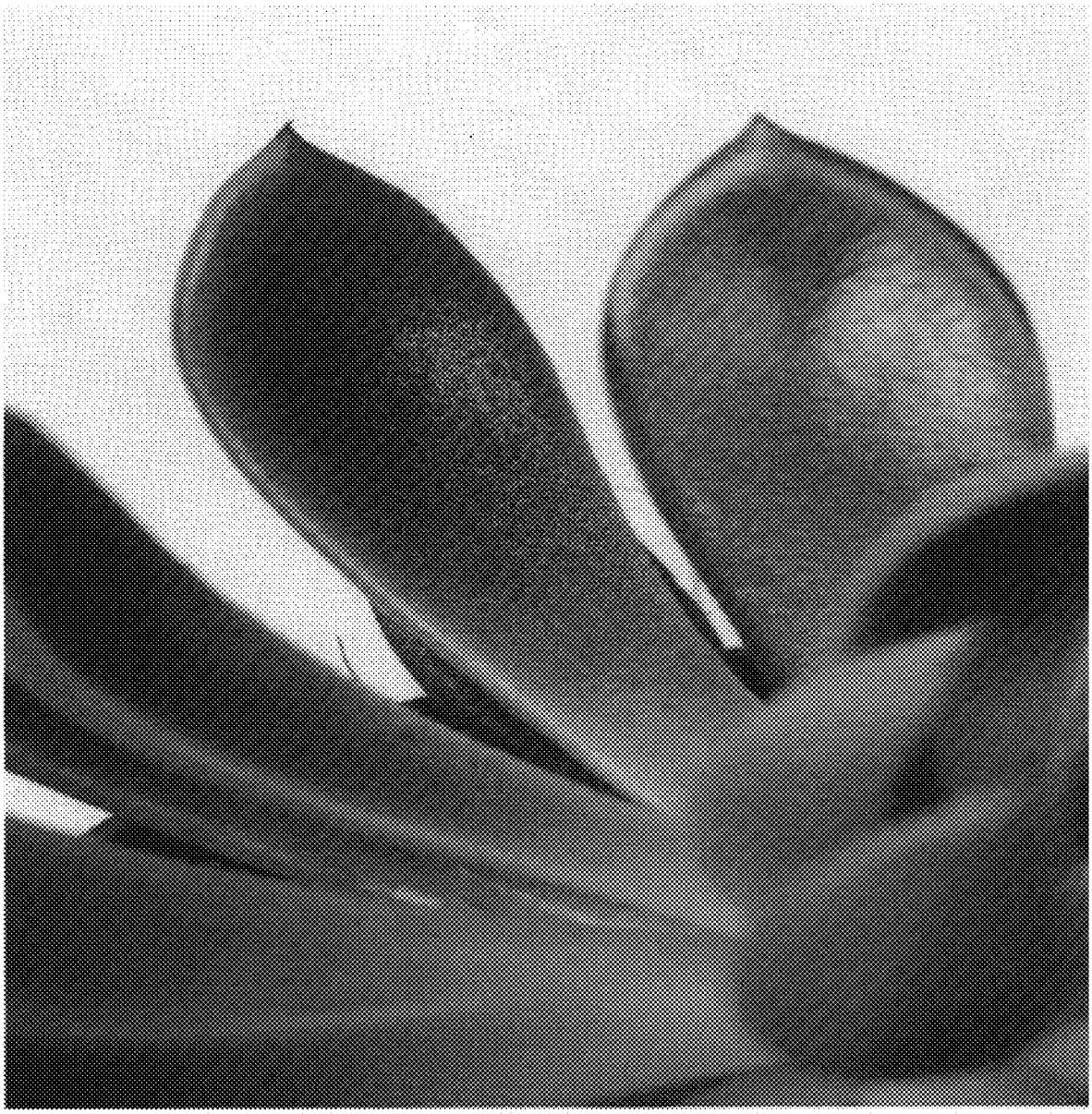
FIG. 3 illustrates, as nearly true as it is reasonably possible to make the same in color photographs of this type, the adaxial surface of the mature foliage 'AMIECH2103'.
Figure 4:
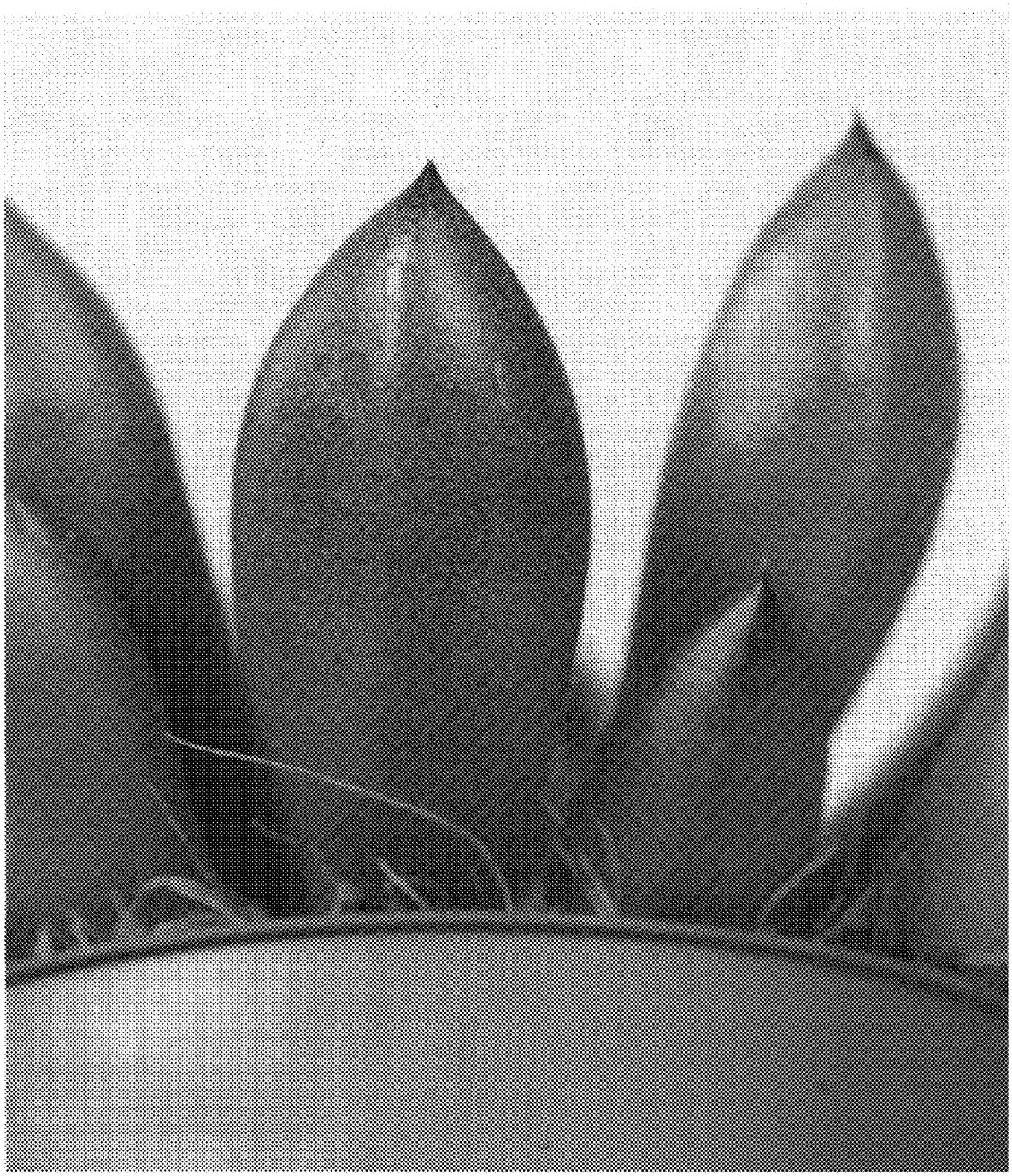
FIG. 4 illustrates, as nearly true as it is reasonably possible to make the same in color photographs of this type, the abaxial surface of the mature foliage 'AMIECH2103'.

The following observations and measurements made in June of 2021 describe averages from a sample set of six specimens of 26 week-old 'AMIECH2103' plants grown in 8.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2103' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2103' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—6.4 cm.

*Plant spread*.—Average of 13.8 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in an 8.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosette, eventually forming a short, unbranched stem with age; no lateral branching.

*Quantity of main stems*.—1.

*Quantity of lateral branches*.—None.

*Main stem dimensions*.—2.0 cm long and 0.9 cm in diameter.

*Internode length*.—0.1 cm.

*Cross section*.—Rounded.

*Aspect*.—Nearly vertical.

*Strength*.—Moderately strong.

*Texture and luster*.—Glabrous, glaucous, and very slightly glossy.

*Color, when developing*.—Yellow-green, nearest to RHS 145B.

*Color of mature stem*.—Yellow-green, nearest to RHS 145B.

*Color at internodes*.—Yellow-green, nearest to RHS 145B.

Foliage:

*Arrangement*.—Rosette.

*Division*.—Simple.

*Attachment*.—Sessile.

*Quantity*.—Approximately 40 leaves per rosette.

*Shape*.—Oblanceolate.

*Dimensions*.—6.7 cm long, 1.6 cm wide, and 0.7 cm thick, on average.

*Aspect*.—Moderately concave and curled upward, distally.

*Attitude*.—Juvenile foliage at the center of the rosette is held upward and outward; foliage becomes progressively more relaxed towards the outer whorls of mature foliage which lay nearly horizontal and curl upward at an average angle of 40 degrees, distally.

*Apex*.—Bluntly acute.

*Base*.—Cuneate.

*Margin*.—Ciliate with very short greyed-green hairs, nearest to RHS 193D, and an average length of 0.2 mm; margins are not undulate.

*Pubescence, texture and luster of the adaxial surface*.—Glabrous with the exception of the margins; smooth and moderately glaucous.

*Pubescence, texture and luster of the abaxial surface*.—Lightly pubescent with very short greyed-green hairs, nearest to RHS 193D, and an average length of 0.2 mm; moderately glaucous.

*Luster of the adaxial surface*.—Moderately glossy.

*Luster of the abaxial surface*.—Moderately glossy.

*Color*.—Juvenile foliage, adaxial surface — Green, nearest to a RHS 137C; tipped and narrowly margined greyed-green, nearest to RHS 193D. Juvenile foliage, abaxial surface — Green, nearest to a RHS 137C; tipped and narrowly margined greyed-green, nearest to RHS 193D. Mature foliage, adaxial surface — Green, nearest to RHS NN137B, and fading to yellow-green towards the base, nearest to RHS 145B; narrowly margined yellow-green, nearest to RHS 145C; tipped greyed-orange, nearest to RHS 166A. Mature foliage, abaxial surface — Green, nearest to a mixture of RHS 138A and 143A, and fading to yellow-green towards the base, nearest to RHS 147D; narrowly margined grey-brown, nearest to N199B; tipped brown, nearest to RHS 200B.

Venation, adaxial surface — No visible venation.
Venation, abaxial surface — No visible venation.
*Petiole*.—No petiole; leaves are sessile.
Inflorescence: No flowering has been observed to date.

Comparisons With the Parent Plants and Closest Known Comparator

Plants of the new cultivar 'AMIECH2103' differ from the seed parent, an *Echeveria setosa* 'Oliver' plant (not patented), in the following characteristics described in Table 1 below. *Echeveria setosa* 'Oliver' plant (not patented), the seed parent, with an unnamed *Echeveria purpusorum* plant (not patented), the pollen parent.

TABLE 1

| Characteristic | 'AMIECH2103' | The seed parent. |
|---|---|---|
| Foliage abundance. | Less abundant than the seed parent. | More abundant than 'AMIECH2103'. |
| Foliar margins. | Ciliate. | Entire. |
| Pubescence of abaxial. leaf surface. | Lightly pubescent. | Glabrous. |
| General coloration of the foliage. | A darker shade of green, relative to the seed parent. | A lighter shade of green, relative to 'AMIECH2103'. |

Plants of the new cultivar 'AMIECH2103' differ from the pollen parent, an unnamed *Echeveria purpusorum* plant (not patented), in the following characteristics described in Table 2 below.

TABLE 2

| Characteristic | 'AMIECH2103' | The pollen parent. |
|---|---|---|
| Foliage length. | Longer than the pollen parent. | Shorter than 'AMIECH2103'. |

TABLE 2-continued

| Characteristic | 'AMIECH2103' | The pollen parent. |
|---|---|---|
| Foliage attitude. | Conspicuously curled upward, distally. | Either not curled upward or only slightly curled upward, distally. |
| General coloration of the foliage | Dark green. | A lighter shade of green, relative to 'AMIECH2103' and suffused with brown. |

Comparisons With the Closest Known Comparator

Plants of the new cultivar 'AMIECH2103' differ from the closest known commercial comparator, *Echeveria* 'Serrana' (not patented), in the following characteristics described in Table 3 below.

TABLE 3

| Characteristic | 'AMIECH2103' | 'Serrana' |
|---|---|---|
| Foliage attitude. | Conspicuously curled upward, distally. | Either not curled upward or only slightly curled upward, distally. |
| General coloration of the mature foliage | Green and tipped greyed-orange to brown. | Green and heavily suffused with a mixture of very dark brown and greyed-purple; tipped black. |

That which is claimed is:

1. A new and distinct variety of *Echeveria setosa* 'Oliver' x *Echeveria purpusorum* A. Berger plant named 'AMIECH2103', substantially as described and illustrated herein.

* * * * *